United States Patent [19]
Lee et al.

[11] Patent Number: 5,395,919
[45] Date of Patent: Mar. 7, 1995

[54] POLY-β-HYDROXY ALKANOATE (PHA) COPOLYMER, METHOD OF ITS PRODUCTION, THE MICROBE WHICH PRODUCES IT, AND PHA COPOLYMER BLEND

[75] Inventors: Yang-Gul Lee; Guhn-Been Yim, both of Seoul, Rep. of Korea

[73] Assignee: KOHAP, Ltd., Seoul, Rep. of Korea

[21] Appl. No.: 122,590

[22] PCT Filed: Sep. 16, 1991

[86] PCT No.: PCT/KR91/00019
§ 371 Date: Nov. 18, 1993
§ 102(e) Date: Nov. 18, 1993

[87] PCT Pub. No.: WO92/18553
PCT Pub. Date: Oct. 29, 1992

[30] Foreign Application Priority Data
Apr. 9, 1991 [KR] Rep. of Korea ............. 1991-5607

[51] Int. Cl.$^6$ ............. C08G 63/06; C12P 7/62
[52] U.S. Cl. ............. 528/361; 435/135; 435/253.3; 435/874
[58] Field of Search ............. 528/354, 357, 361; 435/135, 253.3, 874

[56] References Cited
U.S. PATENT DOCUMENTS
5,135,859  8/1992  Witholt et al. ............. 435/135

Primary Examiner—John Kight, III
Assistant Examiner—Shelley A. Dodson
Attorney, Agent, or Firm—Watson, Cole, Grindle & Watson

[57] ABSTRACT

A new poly-β-hydroxy alkanoate (PHA) copolymer is produced in the cell of *Pseudomonas cepacia* KYG-505 (KCCM 10004) and a variety of polymer blends of PHB and PHA are developed, The PHA copolymer can improve the properties of known PHB through blending and, having double bonds on some of its side chains, exhibits capabilities for organic synthesis, whereby it useful in production of polymers with various properties and biodegradability.

9 Claims, 8 Drawing Sheets

□ Saturated Monomer
+ Unsaturated Monomer
Number of carbon

FIG.8 molecular weights

□ Before Precipit.  + After Precipit.

POLY-β-HYDROXY ALKANOATE (PHA) COPOLYMER, METHOD OF ITS PRODUCTION, THE MICROBE WHICH PRODUCES IT, AND PHA COPOLYMER BLEND

FIELD OF ART

The invention is related to a method of aerobic production of poly-β-hydroxy alkanoate copolymer (PHA, hereinafter) in the living cell of a microbe by restraining supply of nutrients.

The polyester PHA produced by the microorganisms used in this invention is a copolymer made of β-hydroxy carboxylic acid monomers which have various numbers of carbon atoms. Because it has a biodegradability it can be used in production of various films including those for agricultural use, various plastic molds like containers, surgical suture, artificial dermic tissue, packing materials with optical activity, etc.

BACKGROUND ART

In European Patent No. 0,046,344 an art is disclosed of production of poly-β-hydroxy butyrate (PHB) by the use of glucose. It is a technique of producing PHB by accumulating it in a cell by exhausting the source of nitrogen, making use of *A. eutrophus* NCIB 11599, which is a mutant strain of *Alkaligenes eutrophus* H16.

In European Patent No. 0,069,497 is disclosed a method of producing a copolymer of 3 HB (3-hydroxy butyrate) and 3HV (3-hydroxy valerate), which is the main constituent of PHB homo-polymer, by making use of organic acids such as propionic acid and glucose as carbon sources of *A. eutrophus* NCIB 11599. This copolymer is useful by changing the processability and various properties of PHB as well as lowering its degree of crystallization by the integration of 3HV elements in the molecular chain of PHB homopolymer.

In Japanese Patent Laid-open No. Sho 64-269989, Sho 64-48821, Hei 1-156320 are disclosed the methods producing several types of new copolymers in which 5HV (5-hydroxy valerate), 3HV (3-hydroxy valerate) and 4HB (4-hydroxy butyrate) are bonded together making use of *A. eutrophus*, with a view to the improvement of the mechanical properties of PHB.

In production of these improved copolymers, glucose and organic acids need to be used simultaneously, and in order to increase the contents of these copolymers it is required to increase the broth concentration of organic acids toxic to cells, whereby resulting in a remarkably lowered productivity of the copolymers, while the high price of glucose debases the economic advantages of this technique.

Again, European Patent No. 0,052,460 has disclosed the method of production of an improved PHB blend, with the view to the improvement of the mechanical properties of PHB, by means of blending PHB and non-biodegradable synthetic polymer, but this has a demerit in lowering bio-degradability of the blend which is the most important advantage of PHB indeed, because of containing the non-biodegradable synthetic polymer. Meanwhile Japanese Patent Laid-open No. Sho 63-226291 has disclosed a way of production of polyester copolymer making use of *Pseudomonas oleovoran* bacteria with saturated or unsaturated hydrocarbon (paraffin, olefin) as the carbon sources. This copolymer is a polymer from polyester bondings of 3-hydroxy carboxylic acids having 6 to 12 carbon atoms. Because of the poor contents of polyester accumulated and produced in the cells by restraining of nutrients, its productivity is extremely low.

In view of these, the development of a biodegradable polyester with lower degree of crystallization to help with the improvement of the properties of PHB is required, and so is the development of a process for raising the productivity of polyester with low degree of crystallization and yet biodegrable.

In *J. Gen. Appl. Microbio*, 1983, Vol. 29, pp 17–40, by Oyaizu et al it was made clear that various microorganisms of Pseudomonas genus have specificity in compositions of fatty acids and 3-hydroxy fatty acids in cells. According to Fulco's *Prog. Lipid Res.*, 1983, Vol. 22, pp 133–160, 3-hydroxy fatty acids are widely distributed in most gram-negative bacteria; according to the biosynthetic process of PHA copolymer in oleovoran species. Introduced by Witholt et al in *Appl. Environ. Microbiol.*, 1988, Vol. 54, No. 12 pp 2924–2932, 3-hydroxy fatty acids were polymerized by the action of acyl-CoA synthetase and PHA synthetase. These discoveries can mean that such PHA copolymers, composed of 3-hydroxy carboxylic acids having carbon atoms, ranging over C4–C16, can be produced by microorganisms.

For example, according to *Biotechnology letters*, 1989, Vol. 11, No. 7, pp 471–476, by Dawes et al, *P. putida, P. oelovoran, P. aeroginosa, P. flourescence*, and other species in Pseudomonas genus produce PHA polyester copolymer of 3-hydroxy acid with C6~C10 making use of alkane, alkanol, and alkanoic acids. But these bacteria do not use rapidly assimilated carbohydrates, such as glucose, fructose, sucrose in production of PHA, whereupon their productivity is low.

BRIEF DESCRIPTION OF THE DRAWINGS

FIG. 2 shows the GC spectrum of PHA copolymer. After the methyl esterification, GC analysis of PHA showed that each peak is methyl ester form of monomers which compose PHA.

FIG. 4 (a) shows the CI (chemical ionization) mass spectrum of 3-hydroxy dodecanoate methyl ester (3DDA). It is seen that the molecular weight is $231-1=230$, and the 213 peak is a result of the dehydration from a 3DDA molecule.

FIG. 4 (b) shows the CI mass spectrum of 3-hydroxy-10-dodecenoate methyl ester (3DDE). It is seen that the molecular weight is $229-1=228$, and the 211 peak is a result of the dehydration from a 3DDE molecule.

FIG. 5 (a) shows the EI (electronic ionization) mass spectrum of 3-hydroxy dodecenoate methyl ester (3DDE).

FIG. 5 (b) shows the EI mass spectrum of 3-hydroxy-10-dodecenoate methyl ester (3DDE).

FIG. 7 (a) shows the IR spectrum of PHB.

FIG. 7 (b) shows the IR spectrum of PHA copolymer.

DESCRIPTION OF INVENTION

The present invention is intended to culture microorganism of Pseudomonas cepacia species aerobically and, by means of controlling nutrients like nitrogen sources, to produce PHA polyester copolymer of 3-hydroxy carboxylic acid having 4~14 carbon atoms, in cells.

In prior arts, emphasis was placed upon the improvement of the properties and processability of PHB, and organic acids toxic to cells were used in production of copolymers, resulting in remarkable decrease in their productivity, compared to production of PHB homopolymers. As it is in the case with Japanese Patent Laid-open No. Sho 63-226291, saturated or unsaturated hydrocarbons were used as carbon sources which caused the growth of cells and productivity of PHA low. In contrast, in the present invention a new process with higher productivity has been developed for manufacturing copolymers of 3-hydroxy carboxylic acids with a large number of carbons by the use of carbohydrates with a capacity of quick assimilation such as sucrose, glucose, fructose, glycerol, etc. as sources of carbon. The resulting PHA copolymer has low crystallinity, so it can either replace the existing PHB or, by the use of polymer blending techniques, can be used profitably for the improvement of PHB properties.

(1) Monomer composition of copolymer

The method in the present invention is one with high productivity in which such carbohydrates as sucrose, glucose, fructose, glycerol, etc. as well as such complex carbohydrates as molasses are used as the common carbon sources for the growth of cells and for production of PHA copolymer alike, and the structure of the copolymer produced by that method is as follows:

n = 2, 4, 6, 8, 10 and m = 0, 2, 4, 6, 8

The copolymer produced by the present invention is a polymer of polyester bondings with, as its monomer, 3-hydroxy carboxylic acids having carbon atoms, ranging over C4, C6, C8, C10, C12, and C14 and also 3-hydroxy carboxylic acids having carbon atoms C6, C8, C10, C12, and C14 containing a double bond placed in the position of ω2 on its side chain.

(2) Strains used

The strains used in the present invention belong to cepacia species of Pseudomonas genus according to Bergy's Manual of Determinitive Bacteriology (by N. R. Krieg and J. G. Holt). However, according to J. Gen. Appl. Microbiol. Vol. 29, pp. 17–40 (by Oyaiz et al), in which classification of species of Pseudomonas genus is made by the different composition of the fatty acids and 3-hydroxy fatty acids in the cells, however, it is different from the cepacia species in that it produces 3-hydroxy decanoates and 3-hydroxy dodecanoates together, though it corresponds with the *cepacia* species in that it produces 3-hydroxy tetradecanoates.

*Pseudomonas cepacia* KYG-505, which was the strain used in the present invention, was deposited with Korean Culture Center of Microorganisms, Department of Food Engineering, College of Eng., Yonsei University at Sodaemun-gu, Seoul 120-749, Korea on Nov. 29, 1990 and its accession number is KCCM-10004.

*Pseudomonas cepacia* KYG-505 is obtained by collecting a sample from waste water from textile mills, diluting it with 0.85% (W/V) NaCl solution to $10^4$–$10^5$ times as much, and spreading this diluted sample on an agar culture medium of enzyme extract, and it has such bacteriological characteristics as are given below:

<Sources of strain separation>
Waste water

<Shape of cells under microscope>
1. Appearance:rod form (diameter 0.7–1.1 μm, length 1.5–4.0 μm)
2. Flagella:*Peritrichous flagella*
3. Unicellular or bicellular existence
4. Motility:positive
5. Spore formation:negative
6. Gram stain:negative
7. PHB production:positive <Cells' growth in each sort of media>
1. Culture on surface of agar medium with yeast extract
   24 hours at 35° C.
   Degree of rise:medium
   Surface: flat, or low semi-spherical
   Size of colony:1–3 mm
   Color of colony:white
   Transparency:low
   PHA production
2. Culture in medium of yeast extract
   24 hours at 35° C.
   Speed of growth: very fast, only unicellular existence
   Color of culture broth: yellow earlier and brown later
   PHA production
3. Culture on surface of agar medium containing sucrose
   48 hours at 35° C.
   Degree of rise:low
   Surface:flat, or low semi-spherical
   Size of colony:0.5–1.5 mm
   Color of colony:white
   Transparency:low
   PHA production
4. Culture in synthetic medium containing sucrose 24 hours at 35° C.

Speed of growth: fast, uni- and bi-cellular existence

Color of culture broth: white earlier and light brown toward the end

PHA production

<Physiological characteristics>

1. Catalase:positive
2. Oxidase:positive
3. Urease:positive
4. Nitrate reduction:negative
5. Levan formation from sucrose:negative
6. Gelatin hydrolysis:positive
7. Starch hydrolysis:negative
8. PHB hydrolysis outside cells:negative
9. Denitrification:negative
10. Generation of pigments:yellow earlier and brown later
11. Assimilation of nitrogen source:making use of ammonium salts and urea
12. Property toward oxygen:aerobic
13. PH to grow: grow in PH 4–9; most preferable in PH 6.5–7.0
14. Growth temperature:10°–40° C.; 30°–35° C. most preferable
15. G+C elements content:67.0–67.5 mol %
16. Carbon sources convertibility and production of PHA

| Carbon Sources | Assimilation | PHA Production |
|---|---|---|
| fructose | +++ | yes |
| glucose | +++ | yes |
| sucrose | +++ | yes |
| lactose | − | yes |
| maltose | + | yes |
| mannitol | + | yes |
| sorbitol | + | yes |
| starch | − | yes |
| propionate | + | yes |
| butyrate | + | yes |
| valerate | + | yes |
| acetate | ++ | yes |
| phthalate | − | yes |
| formate | − | yes |
| citrate | +++ | yes |
| maleate | − | yes |
| lactate | +++ | yes |
| L-glutamate | +++ | yes |
| L-glycine | − | yes |
| L-histidine | +++ | yes |
| L-asparagine | +++ | yes |
| L-methionine | − | yes |
| methanol | − | yes |
| ethanol | ++ | yes |
| n-propanol | ++ | yes |
| iso-propanol | − | yes |
| n-butanol | ++ | yes |
| iso-butanol | − | yes |
| ethylene glycol | − | yes |
| propylene glycol | ++ | yes |
| glycerol | +++ | yes |
| myo-inositol | + | yes |
| phenol | − | yes |
| bitaine | − | yes |
| pantothenate | ++ | yes |

(3) Analysis of PHA

Figure 1:
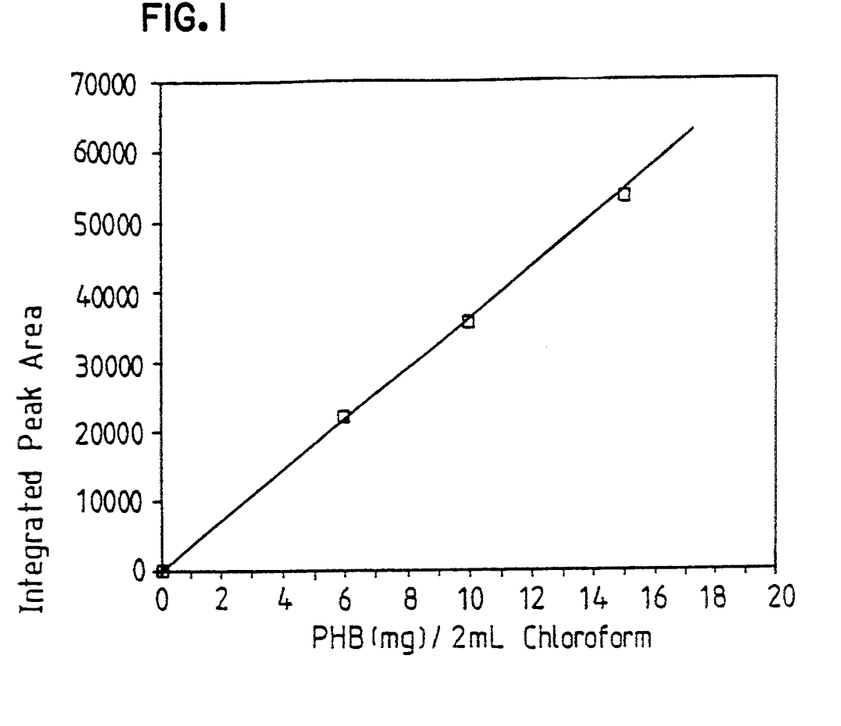
FIG. 1 gives a correlation line of the standard quantity of PHB for the quantity of PHA copolymer. For the determination of the PHA quantity, PHB was utilized as the standard sample; the GC spectrum was analyzed, and the areas measured were calculated to obtain the quantity of PHA.

For analysis of GC and GC-mass spectrum, samples were prepared by treatment of PHA in the way given by Braunegg et al in *Eur. J. Microbiol. Biotechnol.*, Vol. 6 (pp 29–37). For a quantitative analysis PHB was used as the standard material, and the correlation line between PHB quantity and peaks area on the GC spectrum is shown in FIG. 1.

Figure 2:
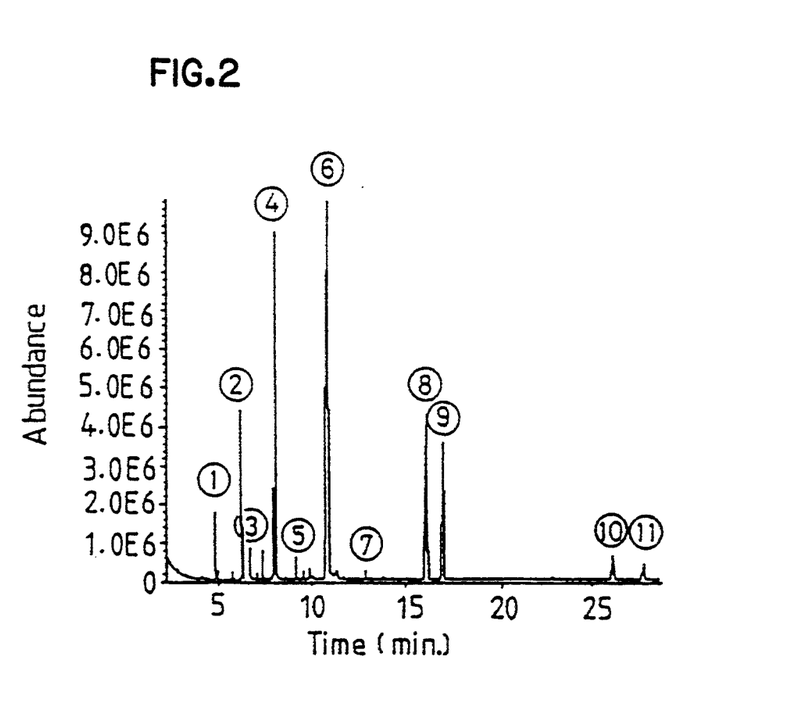

FIG. 2 being a result of PHA analysis on GC spectrum, peaks 1, 2, 4, 6, 8, and 10 stand for 3-hydroxy carboxylic acids having 4, 6, 8, 10, 12, and 14 carbons, monomers of such general compositions as is given in the following formula.

n = 0, 2, 4, 6, 8, 10

Peaks 3, 5, 7, 9, and 11 stand for 3-hydroxy carboxylic acids respectively having 6, 8, 10, 12, and 14 carbons, that is, such monomers having a double bond in the position of ω2 on its side chain as given in the following general formula.

m = 0, 2, 4, 6, 8

The formula and names of each peak are given in Table 1 below.

Figure 3:
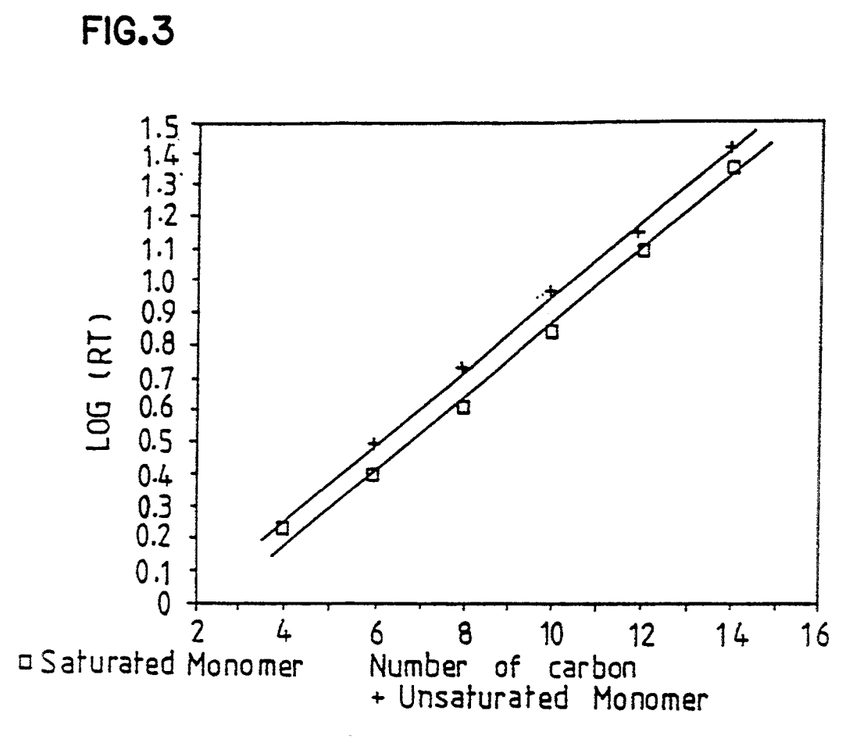
FIG. 3 shows the correlations between the log value of the retention time (RT) and the number of carbons of each monomer of PHA copolymer on the GC spectrum, indicating that the log value of RT gives linear relation with number of carbons.

The correlation between the log value of the retention time on GC spectrum at each peak and the number of carbons is in FIG. 3, and it is known that the retention time according to the number of carbons shows periodicity. Each other peaks on the GC spectrum is supposed to indicate the organic acids or its derivatives which block the OH groups at the end of PHA.

TABLE 1

| Peak No. | Components of PHA | | Mol. wgt. | Abbr. |
|---|---|---|---|---|
| | Formula | Monomer | | |
| 1 | HOCHCH$_2$COCH$_3$ \| CH$_3$ (O double bond) | 3-hydroxy butyrate | 118 | 3HB |
| 2 | HOCHCH$_2$COCH$_3$ \| (CH$_2$)$_2$CH$_3$ (O double bond) | 3-Hydroxy hexanoate | 146 | 3HA |
| 3 | HOCHCH$_2$COCH$_3$ \| CH=CHCH$_3$ (O double bond) | 3-hydroxy-4-hexenoate | 144 | 3HE |
| 4 | HOCHCH$_2$COCH$_3$ \| (CH$_2$)$_4$CH$_3$ (O double bond) | 3-hydroxy octanoate | 174 | 3OA |
| 5 | HOCHCH$_2$COCH$_3$ \| (CH$_2$)$_2$CH=CHCH$_3$ (O double bond) | 3-hydroxy-6-octenoate | 172 | 3OE |
| 6 | HOCHCH$_2$COCH$_3$ \| (CH$_2$)$_6$CH$_3$ (O double bond) | 3-hydroxy decanoate | 202 | 3DA |

TABLE 1-continued

Components of PHA

| Peak No. | Formula | Monomer | Mol. wgt. | Abbr. |
|---|---|---|---|---|
| 7 | $\text{HOCHCH}_2\overset{\text{O}}{\underset{\|}{\text{C}}}\text{OCH}_3$<br>$\|$<br>$(\text{CH}_2)_4\text{CH}=\text{CHCH}_3$ | 3-hydroxy-8-decenoate | 200 | 3DE |
| 8 | $\text{HOCHCH}_2\overset{\text{O}}{\underset{\|}{\text{C}}}\text{OCH}_3$<br>$\|$<br>$(\text{CH}_2)_8\text{CH}_3$ | 3-hydroxy dodecanoate | 230 | 3DDA |
| 9 | $\text{HOCHCH}_2\overset{\text{O}}{\underset{\|}{\text{C}}}\text{OCH}_3$<br>$\|$<br>$(\text{CH}_2)_6\text{CH}=\text{CHCH}_3$ | 3-hydroxy-10-dodecenoate | 228 | 3DDE |
| 10 | $\text{HOCHCH}_2\overset{\text{O}}{\underset{\|}{\text{C}}}\text{OCH}_3$<br>$\|$<br>$(\text{CH}_2)_{10}\text{CH}_3$ | 3-hydroxy tetradecanoate | 258 | 3TA |
| 11 | $\text{HOCHCH}_2\overset{\text{O}}{\underset{\|}{\text{C}}}\text{OCH}_3$<br>$\|$<br>$(\text{CH}_2)_8\text{CH}=\text{CHCH}_3$ | 3-hydroxy-12-tetradecenoate | 256 | 3TE |

(3) Analysis of PHA copolymer structure

Figure 4A:
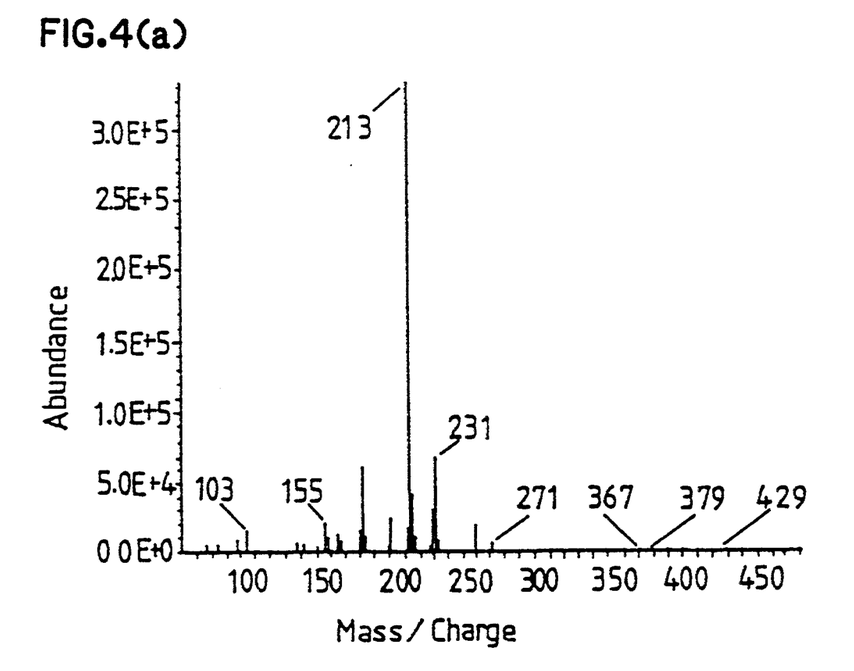
Figure 4B:
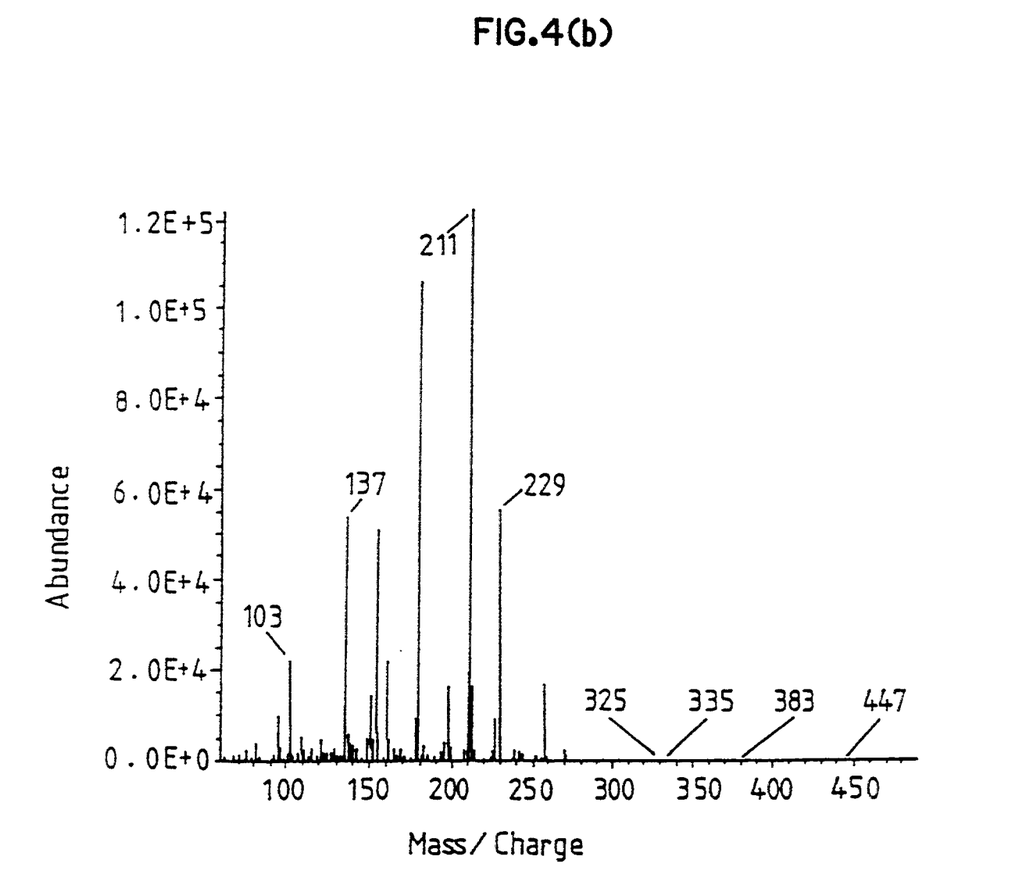

FIG. 4 shows a mass spectrum of 3DDA and 3DDE upon chemical ionization.

Figure 5A:
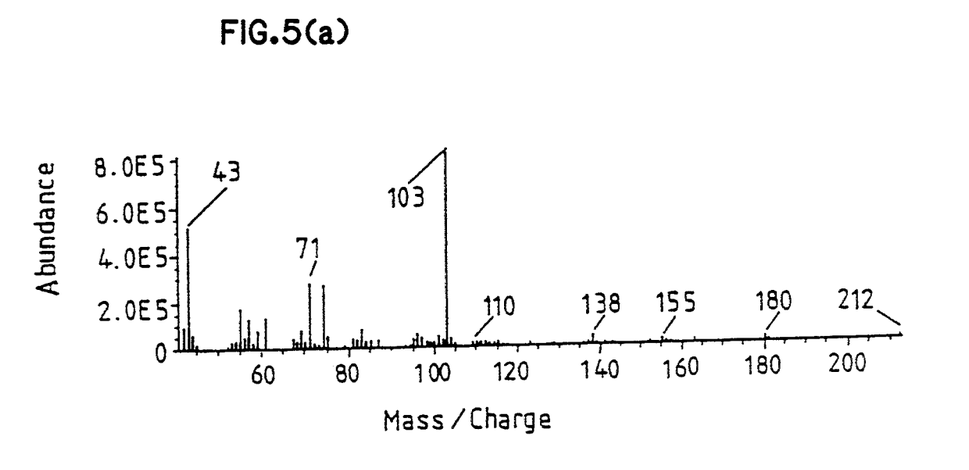
Figure 5B:
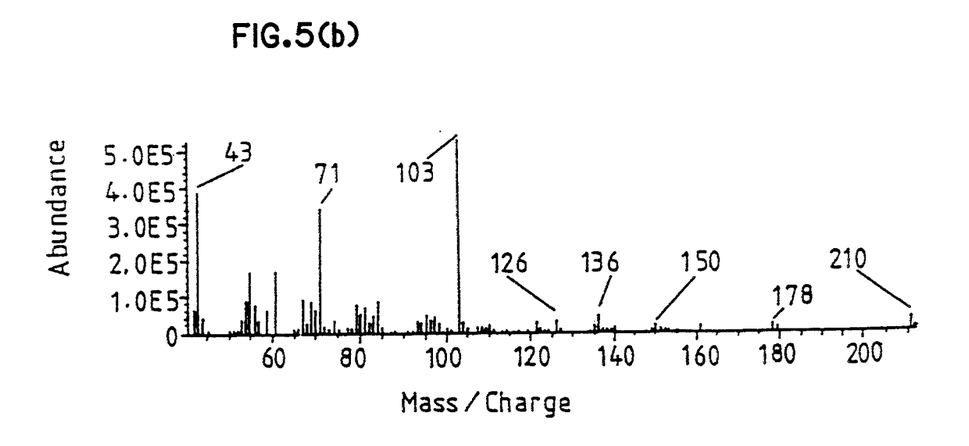

FIG. 4, (a) shows the molecular weight of 230, but (b) shows of 228. In FIG. 5, both (a) and (b) respectively show the mass spectrum of 3DDA and 3DDE upon electronic ionization, both (a) and (b) include peaks (m/e=138, 136; m/e=180,178: m/e=212,210) with difference in molecular weights by 2 meaning decrease of molecular weight on account of double bonds.

The peak m/e=126 in (b) of FIG. 5 signifies the side chain of 3DDE having a double bond, and every component of PHA, by mass spectrum, shows peaks 103(HOCHCH$_2$ COOCH$_3$), or 74(CH$_2$ COOCH$_3$), 43(OHCHCH$_2$) in common.

Figure 6:
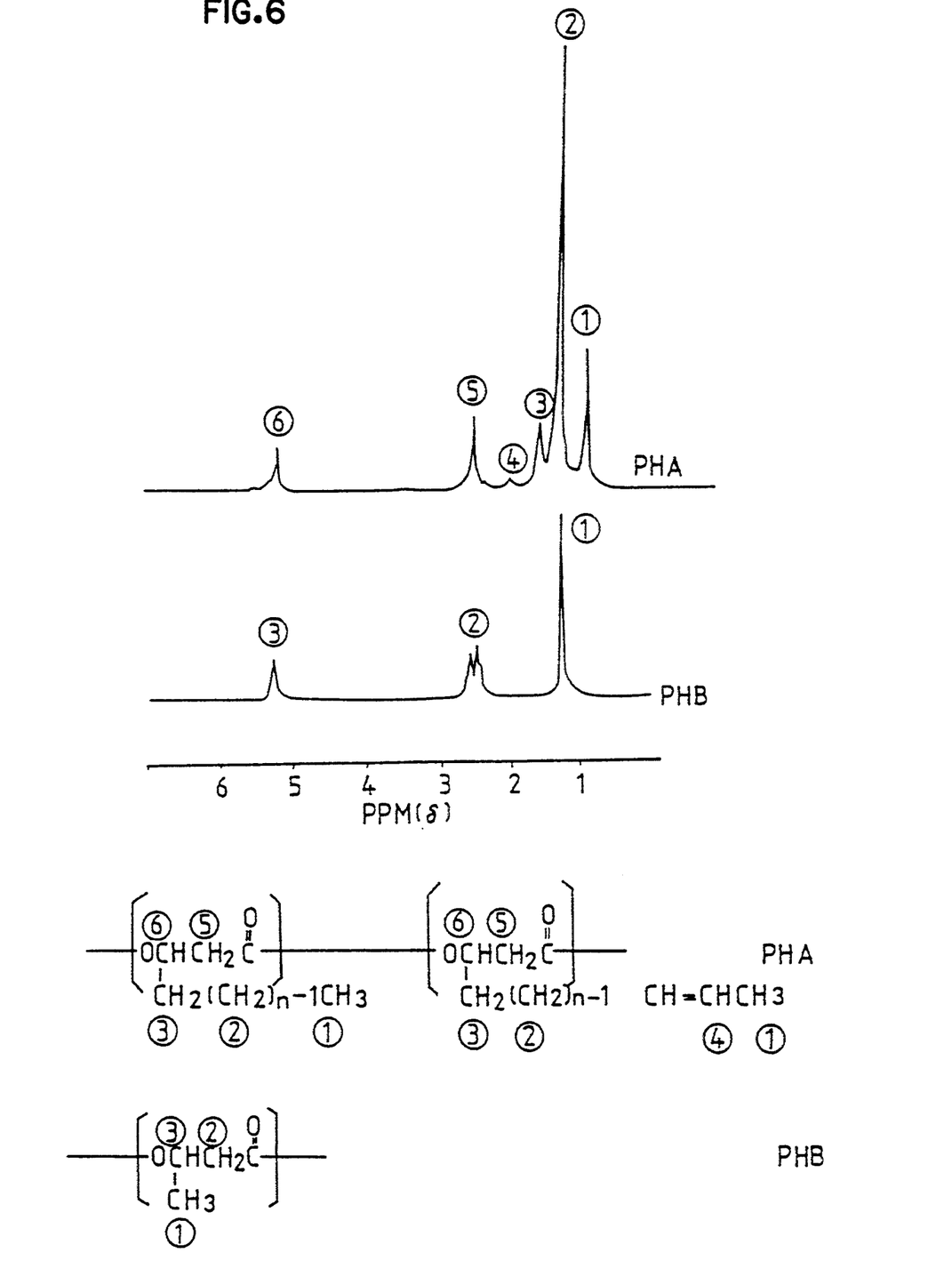
FIG. 6 shows 'H-NMR spectrum of a PHA copolymer.

NMR spectrum is shown in FIG. 6, together with PHB spectrum. Compared with PHB, the peaks of hydrogen atoms on the side chain appear separated in three; δ=0.91, 1.27, 1.59 ppm, and especially the peak of hydrogen atoms of the vinyl group having a double bond on the side chain stands at δ=2.05.

Figure 7A:
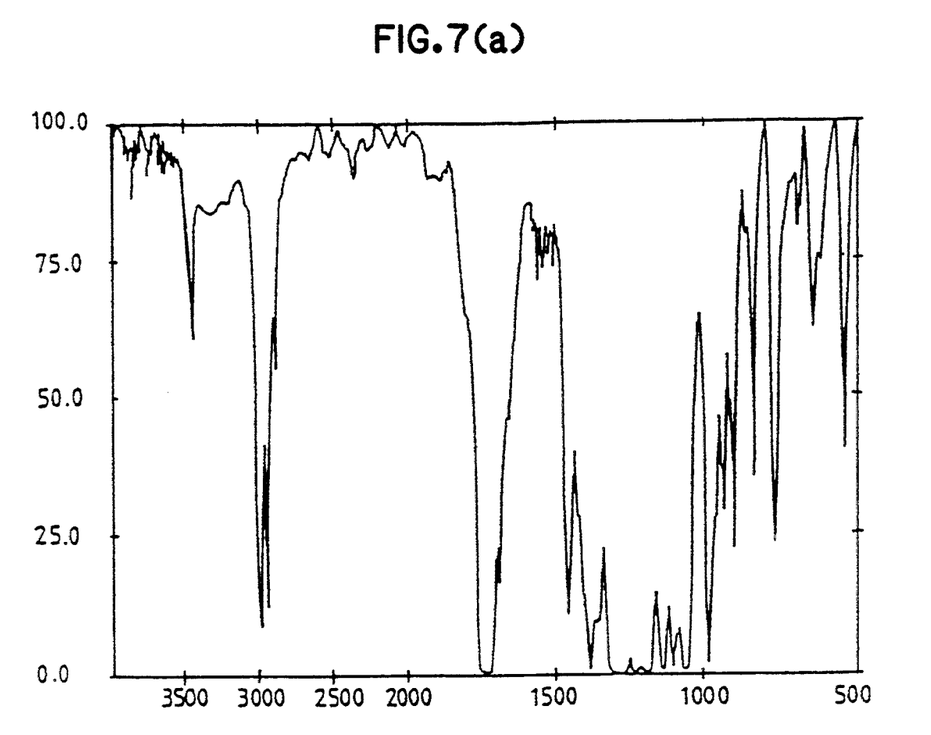
Figure 7B:
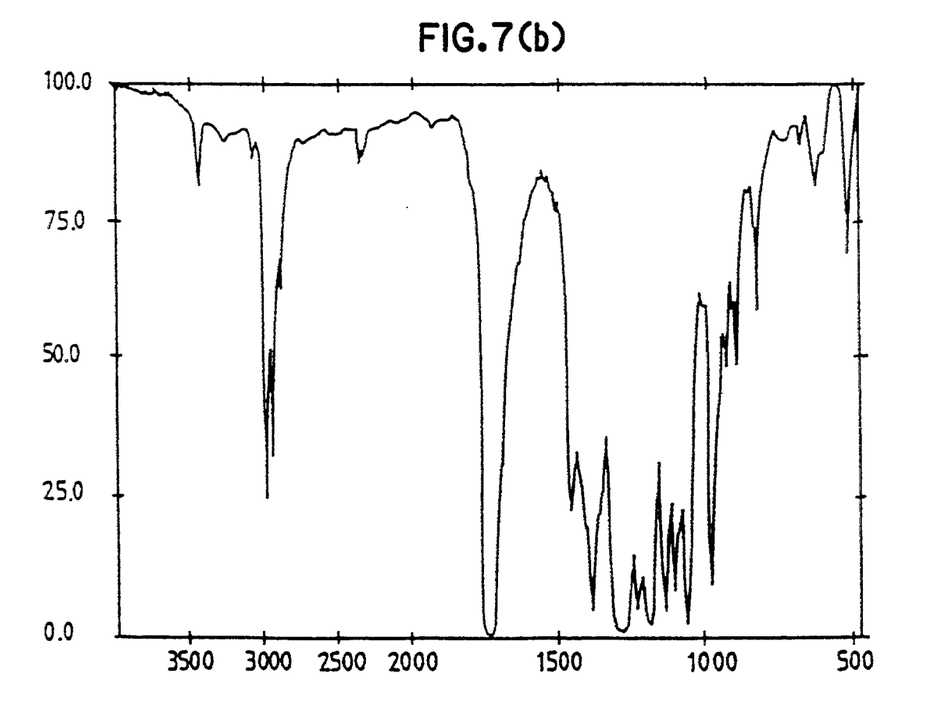

IR spectra are given in FIG. 7, (a) for PHB and (b) for PHA. In both cases, it appears that an ester carbonyl band at 1725 cm$^{-1}$, methyl and methylene bands at 2850-3000 cm$^{-1}$, and in (b) a double bond band on the side chain at 3080 cm$^{-1}$.

(4) Conditions for cell growth and PHA production

In all the experiments, Psuedomonas cepacia KYC-505(KCCM 10004) was used. For the growth of the cells, carbon sources, nitrogen sources, and such salts as P, Mg, K, Na, etc. along with Fe, Mn, Co, Ca, Cu, Zn and other trace elements are necessary.

Aside from these nutrients, supply of oxygen is required for an aerobic growth, the optimum PH being 6.5–7.0 and the optimum temperature for their growth 30°–35° C. The carbon sources which can be used include such carbohydrates as sucrose, fructose, glucose, maltose, such alcohols as ethanol, glycerol, n-propanol, n-butanol, propylene glycol, such organic acids as acetate, propionate, butyrate, valerate, lactate, citrate, etc., and such amino acids as glutamate, histidine, asparagine, etc. For complex carbon sources, fish oil, molasses, yeast extract and others are available.

For nitrogen sources, such ammonium salts as ammonium sulfate, ammonium chloride, ammonium hydroxide, ammonia water and urea and complex nitrogen sources can be used.

Production and accumulation of PHA copolymer in the cells begin at exhaustion of one or more sorts of nutrient sources in a medium, and in general the exhaustion of nitrogen sources results in the highest degree of accumulation. Because PHA is a source of energy and storage of carbon, it is reused in the process of metabolism and will decrease in it's intercellular content when the carbon source in the medium is exhausted; therefore, it is necessary to keep sufficient carbon source in the medium and then restrain the nitrogen source to induce production and accumulation of PHA.

For a continuous culture and preservation, the cells were cultured at 35° C. in a YM medium of the following composition:

| The YM medium | yeast extract | 3 g/L |
|---|---|---|
| | malt extract | 3 g/L |
| | trypton | 5 g/L |
| | sucrose | 5 g/L |

The cell culture was performed for 12–24 hours in 1 L of shaking flask inside a shaker with 150–200 rpm, of 200 mL of a growth medium of the following composition at 35° C.:

| KH$_2$PO$_4$ | 1 g/L |
|---|---|
| Na$_2$HPO$_4$12H$_2$O | 3.0 g/L |
| MgSO$_4$ | 0.4 g/L |
| (NH$_4$)$_2$SO$_4$ | 0.5 g/L |
| Trace elements solution | 4 mL/L |

For the carbon source 0.5% (W/V) was used and the composition of the trace element solution was as follows:

| FeSO$_4$7H$_2$O | 3.0 g/L | MnCl$_2$4H$_2$O | 60 mg/L |
|---|---|---|---|
| CaCl$_2$2H$_2$O | 2.5 g/L | CoCl$_2$6H$_2$O | 40 mg/L |
| ZnSO$_4$7H$_2$O | 200 mg/L | CuSO$_4$5H$_2$O | 20 mg/L |
| H$_3$BO$_3$ | 600 mg/L | NiCl$_2$6H$_2$O | 40 mg/L |

In the experiments for production and accumulation of PHA, all the conditions for culturing medium were kept in the same condition as in the case of growing medium, only the concentration of ammonium sulfate were lowered to 0.25 g/L, and after allowing the cells to grow for 12 hours their growth was restrained to lead to an accumulation of PHA. In order to quicken the accumulation of PHA in the cells the concentration of ammonium sulfate must be limited to lower than 0.1 g/L but the carbon source should be kept sufficient. In order to increase the speed of the accumulation sufficient, the medium should be kept at pH 6.5–7.0 and use of potassium phosphate and hydrates of sodium phosphate in a quantity each 1.0–2.0 g/L and 3.0–6.0 g/L respectively, the concentration of MgSO4 and the trace elements kept at 0.2–0.4 g/L and 0.5–4 mL/L respectively.

(5) Separation and purification of PHA

For the separation and purification of PHA accumulated in a cell, there are several methods publicly known. According to the U.S. Pat. Nos. 3,036,959, 3,044,942, and 3,275,610, bacteria are harvested from the broth, washed with acetone to remove some lipids, and thereafter PHA is extracted by means of solutions of chloroform, methylene chloride, pyridine, etc., with some post-treatment to follow.

In the present experiment also similar methods were used for the separation and purification of the PHA accumulated in the bacterial cells, that is, first collecting the cells by centrifugation of 500 g (gravity force) of the culture medium for 10 minutes, washing them with acetone, suspending the bacteria in chloroform well, and then standing them for four to eight hours, whereby to extract the PHA.

The extracted chloroform solution was filtered for removal of remaining cell residues, then precipitants of five to 10 times, as much in volume of chloroform solution, were added to obtain final amorphous PHA copolymer. As precipitants, water, methanol, ethanol, actone, ether, and hexane were tested, and when methanol or ethanol was used amorphous precipitates were found to be deposited. Thereafter, as precipitants in all the process of separation and purification, only methyl alcohol was resorted.

(6) Solution blending of PHB and PHA

In European Patent No. 0,052,460 an improvement on the properties of PHB was achieved by means of blending PHB with synthetic polymers. However, the polymers used as additives being, unlike PHB, non-biodegradable elements, the polymer blend produced has problems in the biodegradability, which is the PHB's greatest merit.

The PHA obtained in the present experiment, unlike PHB with a very high degree of crystallinity, is biodegradable polymer with a very low degree of crystallization, and it helps to obtain further biodegradable polymers of various properties by blending with PHB and controlling its relative content at will.

In the present invention a PHA blend was obtained by adding an adequate quantity of PHB to the chloroform solution which extracted PHA from the bacteria, solving the PHB, and stirring the solution for 10 to 60 minutes at 20° to 100 ° C., then either evaporate off the chloroform or add 5 to 10 times as much as the chloroform solution volume to precipitates to give PHA polymer blend, then filtering, and drying in vacuum at 100° C.

(7) Properties and biodegradability of PHA

Figure 8:
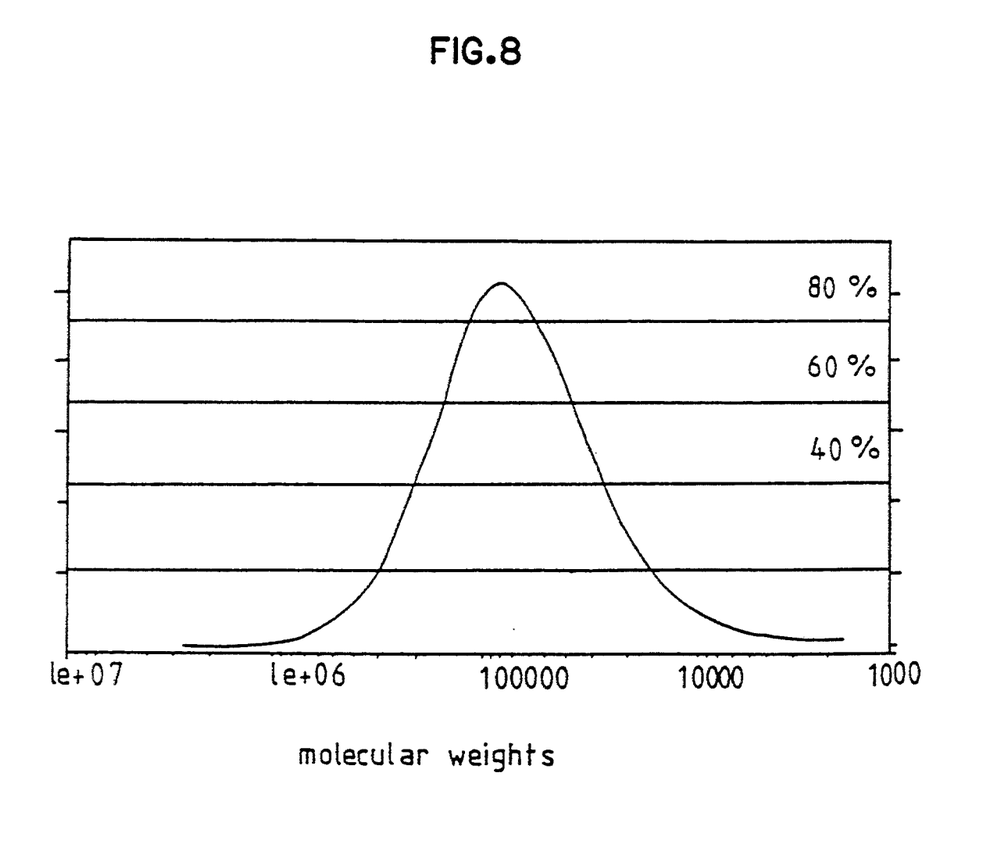
FIG. 8 shows a molecular weight distribution curve of PHA copolymer.

The PHA thus produced is an amorphous polymer with no melting point (Tm) at all. The distribution of molecular weights is given in FIG. 8.

According to *Appl. Environ. Microbiol.*, 1989, Vol. 54, No. 8, pp. 1977–1982 (by Brandle et at), the rate of biodegradation of PHA which has a long side chain, will be slower than that of PHB, as it is claimed.

The PHA obtained in the present experiment is one with a long side chain, and its rate of biodegradation is presumed to be slower than PHB; through a blending with PHB, this rate can be adjusted.

USES IN INDUSTRY

The PHA copolymer obtained in the present invention is a polyester polymer, a polymer similar to known PHB.

PHB, a thermoplastic and biodegradable polymer, can be utilized in the production of various films of agricultural and other usages, molded materials like containers, surgery suture, artificial skin tissue, bone transplantation tissue, packing materials of optical activity, pharmaceutical delivery systems, etc.; however, its poor suitability for processing is a definite demerit.

The PHA obtained in the present invention has an advantage in that it can be blended with PHB to improve the latter's properties for expansion of its scope of usage and at the same time it can be used in the production of a polymer blend which keeps its biodegradability intact.

In other words, the PHA obtained in the present invention is a polymer capable of replacing PHB in all its industrial use, and because some of its monomers have a double bond on their side chains in the position of $\omega 2$, it can bestow functions for a variety of organic chemical variations, thereby making it possible to obtain biodegradable polymers which have various functions.

For description of the present invention in further detail some examples are given below, but it is not restricted following examples.

EXAMPLE 1

By using *Pseudomonas cepacia* KYG-505 (KCCM 10004), 200 ml of the following culture medium with 5 g/L of carbon source and 0.25 g/L of nitrogen source was cultured in a 1L shaking flask for 24 hours:

| | |
|---|---|
| $KH_2PO_4$ | 1 g/L |
| $Na_2HPO_4 12H_2O$ | 3 g/L |
| $(NH_4)_2SO_4$ | 0.25 g/L |
| $MgSO_4$ | 0.4 g/L |
| Trace elements solution | 4 ml/L |

The compositions of the trace elements solution follow;

| | |
|---|---|
| $FeSO_4 7H_2O$ | 3 g/L |
| $CaCl_2 2H_2O$ | 2.5 g/L |
| $ZnSO_4 7H_2O$ | 200 mg/L |
| $H_3BO_3$ | 600 mg/L |
| $MnCl_2 4H_2O$ | 60 mg/L |
| $CoCl_2 6H_2O$ | 400 mg/L |
| $CuSO_4 5H_2O$ | 20 mg/L |
| $NiCl_2 6H_2O$ | 40 mg/L |

The carbon sources experimented with were sucrose, fructose, glucose, maltose, glycerol, molasses, and fish oil; by centrifugation of 100 ml culture broth and washing with acetone it was possible to extract PHA from 20 mg of dried cells and analyse it.

The final concentration of cells and the intracellular content of PHA from every batch with different carbon sources are given in the Table 2:

TABLE 2

| | sucrose | fructose | glucose | maltose |
|---|---|---|---|---|
| Cell Concen- | 2.40 | 2.38 | 2.27 | 0.96 |

TABLE 2-continued

| tration (OD660) | | | | |
|---|---|---|---|---|
| PHA Content | 75 | 72 | 65 | 55 |
| | glycerol | molasses | fish oil | |
| | 2.35 | 2.95 | 2.32 | |
| | 75 | 80 | 83 | |

EXAMPLE 2

Influence of pH on growth of cells and PHA accumulation

*Pseudomonas cepacia* KYG-505 (KCCM 10004) was cultured in the synthetic medium of Example 1, to which were added 5 g/L of sucrose and 0.25 g/L of $(NH_4)_2SO_4$ at pH 4, 5, 6, 7, and 8 respectively for 24 hours. 100 ml of the culture broth from each pH was centrifuged, then washed with acetone, and the PHA was extracted therefrom and analysed.

The final concentration of cells and PHA content at each pH are given in Table 3 below, and the composition of each monomer in the PHA is given in Table 4 below:

Table 5 shows the relative contents of monomers having double bonds as per the varying pHs.

TABLE 3

| Cells' concentration and content of PHA by varying pHs | | | | | |
|---|---|---|---|---|---|
| | pH4 | pH5 | pH6 | pH7 | pH8 |
| Cell concentration (OD660) | 0.80 | 0.77 | 1.09 | 2.59 | 2.28 |
| PHA content (%) | 22.1 | 20.5 | 42.9 | 89.1 | 85.0 |

TABLE 4

| Contents of each monomer at various pHs (wt %) | | | | | |
|---|---|---|---|---|---|
| | pH4 | pH5 | pH6 | pH7 | pH8 |
| 3 HB | 0.12 | 0.12 | 0.07 | 0.18 | 0.09 |
| 3 HA | 4.97 | 5.59 | 3.28 | 3.17 | 3.31 |
| 3 HE | 0.77 | 0.87 | 0.47 | 0.19 | 0.23 |
| 3 OA | 8.69 | 9.07 | 9.70 | 11.86 | 10.69 |
| 3 OE | 1.16 | 1.08 | 0.97 | 0.65 | 0.70 |
| 3 DA | 43.78 | 47.63 | 45.32 | 49.31 | 48.55 |
| 3 DE | 8.26 | 8.42 | 3.65 | 1.46 | 1.60 |
| 3 DDA | 16.50 | 16.64 | 16.04 | 12.02 | 12.28 |
| 3 DDE | 7.45 | 5.06 | 12.61 | 12.14 | 12.60 |
| 3 TA | 0.00 | 0.00 | 3.34 | 2.27 | 2.33 |
| 3 TE | 0.00 | 0.00 | 2.60 | 2.44 | 2.47 |
| Others | 8.30 | 5.52 | 1.95 | 4.31 | 5.15 |

TABLE 5

| Relative contents of double bonds at various pHs (wt %) | | | | | |
|---|---|---|---|---|---|
| | pH4 | pH5 | pH6 | pH7 | pH8 |
| 3HA/3HE | 76.6/13.4 | 76.5/13.5 | 77.5/12.5 | 94.3/5.7 | 93.5/6.5 |
| 3OA/3OE | 88.2/11.8 | 89.4/10.6 | 89.3/10.7 | 94.8/5.2 | 94.0/6.0 |
| 3DA/3DE | 84.1/15.9 | 85.0/15.0 | 92.5/7.5 | 97.1/2.9 | 96.8/3.2 |
| 3DDA/3DDE | 86.9/31.1 | 76.6/23.3 | 71.3/28.7 | 49.8/50.2 | 49.4/50.6 |
| 3TA/3TE | 0.00/0.00 | 0.00/0.00 | 57.2/43.8 | 48.2/51.8 | 48.5/51.5 |

EXAMPLE 3

Effect of $PO_4^{3-}$ on cellular growth and PHA accumulation

*Pseudomonas cepacia* KYG-505 (KCCM 10004) was cultured for 24 hours in a 1L shaking flask of the synthetic culture medium as of Example 1, but the concentration of phosphate ion salts are 0.0, 0.2, 0.5, 1.0, 3.0, and 5.0 times of 1.0 g/L $KH_2PO_4$ and 3.0 g/L $Na_2HPO_4 \cdot 12H_2O$ in each batch flask.

After centrifuging 100 mL of culture solution from each batch with different concentration and washing with acetone, PHA was extracted from 20 mg of dried cells and analyzed.

The final cell concentration and PHA content according to each different concentration of phosphate are given in Table 6, and each PHA element's content given in Table 7.

TABLE 6

| Final cell concentration and PHA content according to various phosphate concentration | | | | | | |
|---|---|---|---|---|---|---|
| | 0.0 | 0.2 | 0.5 | 1.0 | 3.0 | 5.0 (times) |
| Final cell concentration (OD660) | 0.36 | 0.67 | 1.30 | 2.53 | 2.30 | 1.98 |
| PHA content (%) | 75.2 | 46.8 | 59.4 | 85.1 | 79.4 | 80.8 |

TABLE 7

| Contents of each PHA monomer at various phosphate concentration (wt %) | | | | | | |
|---|---|---|---|---|---|---|
| | 0.0 | 0.2 | 0.5 | 1.0 | 3.0 | 5.0 (times) |
| 3HB | 0.08 | 0.24 | 0.49 | 0.51 | 0.12 | 0.20 |
| 3HA | 3.84 | 4.25 | 3.36 | 3.44 | 4.00 | 3.96 |
| 3HE | 0.00 | 0.62 | 0.50 | 0.14 | 0.14 | 0.39 |
| 3OA | 10.90 | 12.87 | 11.12 | 12.45 | 12.35 | 11.52 |
| 3OE | 0.00 | 0.00 | 0.59 | 0.20 | 0.00 | 0.00 |
| 3DA | 49.81 | 45.55 | 46.60 | 48.51 | 48.25 | 46.19 |
| 3DE | 1.97 | 3.68 | 2.92 | 1.46 | 1.75 | 2.14 |
| 3DDA | 14.52 | 14.42 | 14.96 | 11.56 | 12.69 | 12.74 |
| 3DDE | 11.35 | 11.40 | 11.86 | 12.22 | 12.00 | 11.03 |
| 3TA | 4.16 | 2.02 | 2.68 | 2.29 | 2.45 | 2.42 |
| 3TE | 0.00 | 1.63 | 2.69 | 3.14 | 2.35 | 2.05 |
| Others | 3.37 | 3.32 | 2.27 | 4.08 | 3.90 | 7.36 |

EXAMPLE 4

Effect of $MgSO_4$ upon cell growth and PHA accumulation

*Pseudomonas cepacia* KYG-505 (KCCM 10004) was cultured for 24 hours in a 1L shaking flask of the synthetic medium of Example 1, only excluding $MgSO_4$ from it, but adding 5 g/L of sucrose and 0.25 g/L of $(NH_4)_2SO_4$ and make the concentration of $MgSO_4$ respectively 0.0, 0.2, 0.4, 1.0, and 3.0. Then centrifuging 100 mL of the culture medium solution of each batch at different concentration and washing it with acetone; PHA was extracted from 20 mg of dried cells and analyzed.

The final cell concentration and PHA content by each $MgSO_4$ concentration are given in Table 8, and the content of each PHA monomers are given in Table 9.

TABLE 8

| Cell concentration and PHA content at various $MgSO_4$ concentration | | | | | |
|---|---|---|---|---|---|
| | 0.0 g/L | 0.2 g/L | 0.4 g/L | 1.0 g/L | 3.0 g/L |
| Cell concentraton | 1.75 | 2.19 | 2.25 | 2.30 | 1.78 |

TABLE 8-continued

Cell concentration and PHA content at various MgSO4 concentration

|  | 0.0 g/L | 0.2 g/L | 0.4 g/L | 1.0 g/L | 3.0 g/L |
|---|---|---|---|---|---|
| (OD660) | | | | | |
| PHA content (%) | 66.7 | 74.5 | 70.8 | 65.4 | 51.3 |

TABLE 9

Content of each PHA monomer at various MgSO4 concentration (wt %)

|  | 0.0 g/L | 0.2 g/L | 0.4 g/L | 1.0 g/L | 3.0 g/L |
|---|---|---|---|---|---|
| 3HB | 0.14 | 0.15 | 0.18 | 0.11 | 1.17 |
| 3HA | 3.18 | 3.21 | 3.37 | 3.18 | 3.98 |
| 3HE | 0.40 | 0.11 | 0.20 | 0.26 | 0.11 |
| 3OA | 12.01 | 11.45 | 10.90 | 11.43 | 10.10 |
| 3OE | 0.50 | 0.67 | 0.85 | 0.70 | 0.90 |
| 3DA | 49.88 | 50.31 | 49.46 | 50.38 | 48.89 |
| 3DE | 2.50 | 2.45 | 2.56 | 2.24 | 3.21 |
| 3DDA | 11.60 | 11.43 | 10.89 | 11.02 | 11.39 |
| 3DDE | 9.75 | 10.74 | 10.53 | 11.17 | 9.98 |
| 3TA | 2.48 | 2.15 | 2.14 | 1.99 | 1.81 |
| 3TE | 2.24 | 2.09 | 1.75 | 1.86 | 1.77 |
| Others | 5.32 | 5.24 | 7.17 | 5.66 | 6.69 |

EXAMPLE 5

Effect of Trace element on cell growth and PHA accumulation

*Pseudomonas cepacia* KYG-505 (KCCM 10004) was cultured for 24 hours in a 1L shaking flask of the synthetic culture medium of Example 1, only excluding the trace elements, but adding 5.0 g/L of sucrose and 0.25 g/L of $(NH_4)_2SO_4$, and then making the concentration of trace element solutions respectively 0.0, 0.5, 1.5, 4.0, 8.0, and 15.0 mL/L. 100 mL of each solution of various concentration was centrifuged, and washed with acetone, and then PHA was extracted from 20 mg of dried cells and analyzed.

The final cell concentration and PHA content at each various concentration of trace element solution are given in Table 10, and the content of each PHA component is given in Table 11.

TABLE 10

Final Cell concentration and PHA content at various concentration of trace element solution

|  | 0.0 mL/L | 0.5 mL/L | 1.5 mL/L | 4.0 mL/L | 8.0 mL/L | 15.0 mL/L |
|---|---|---|---|---|---|---|
| Final cell concentration (OD660) | 2.38 | 2.43 | 2.33 | 2.35 | 2.20 | 2.15 |
| PHA content (%) | 74.0 | 75.6 | 72.8 | 70.1 | 66.8 | 57.5 |

TABLE 11

Content of each PHA monomer at various Trace element concentration (wt %)

|  | 0.0 mL/L | 0.5 mL/L | 1.5 mL/L | 4.0 mL/L | 8.0 mL/L | 15.0 mL/L |
|---|---|---|---|---|---|---|
| 3HB | 0.10 | 0.10 | 0.13 | 1.01 | 0.09 | 0.10 |
| 3HA | 3.40 | 3.43 | 3.48 | 3.44 | 3.34 | 3.39 |
| 3HE | 0.28 | 0.25 | 0.30 | 0.24 | 0.20 | 0.26 |
| 3OA | 11.57 | 11.56 | 11.78 | 11.94 | 11.57 | 11.43 |
| 3OE | 0.70 | 0.64 | 0.84 | 0.75 | 0.77 | 0.70 |
| 3DA | 51.03 | 50.39 | 50.34 | 49.90 | 50.24 | 50.45 |
| 3DE | 1.78 | 1.68 | 1.95 | 1.97 | 2.09 | 2.15 |
| 3DDA | 12.16 | 12.31 | 12.34 | 12.53 | 12.84 | 12.63 |
| 3DDE | 12.79 | 12.65 | 12.79 | 12.95 | 12.87 | 12.41 |
| 3TA | 2.30 | 2.36 | 2.48 | 2.23 | 2.30 | 2.36 |
| 3TE | 2.42 | 2.18 | 2.37 | 2.43 | 2.10 | 2.56 |
| Others | 1.44 | 2.45 | 1.20 | 0.61 | 1.59 | 1.56 |

EXAMPLE 6

Figure 9:
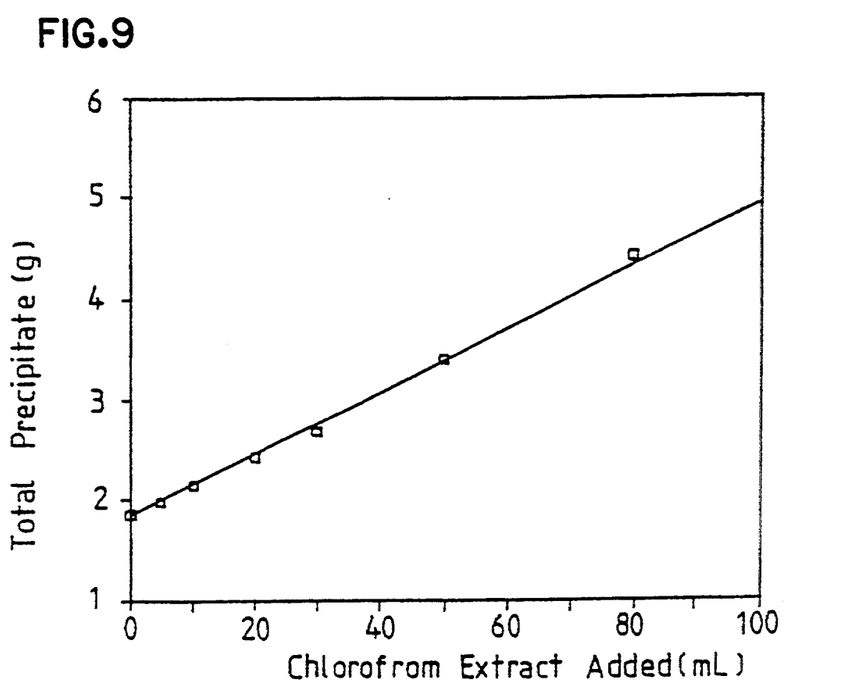
FIG. 9 shows that the quantity of PHA copolymer precipitated is proportionate to the added chloroform extract of PHA copolymer.
Figure 10:
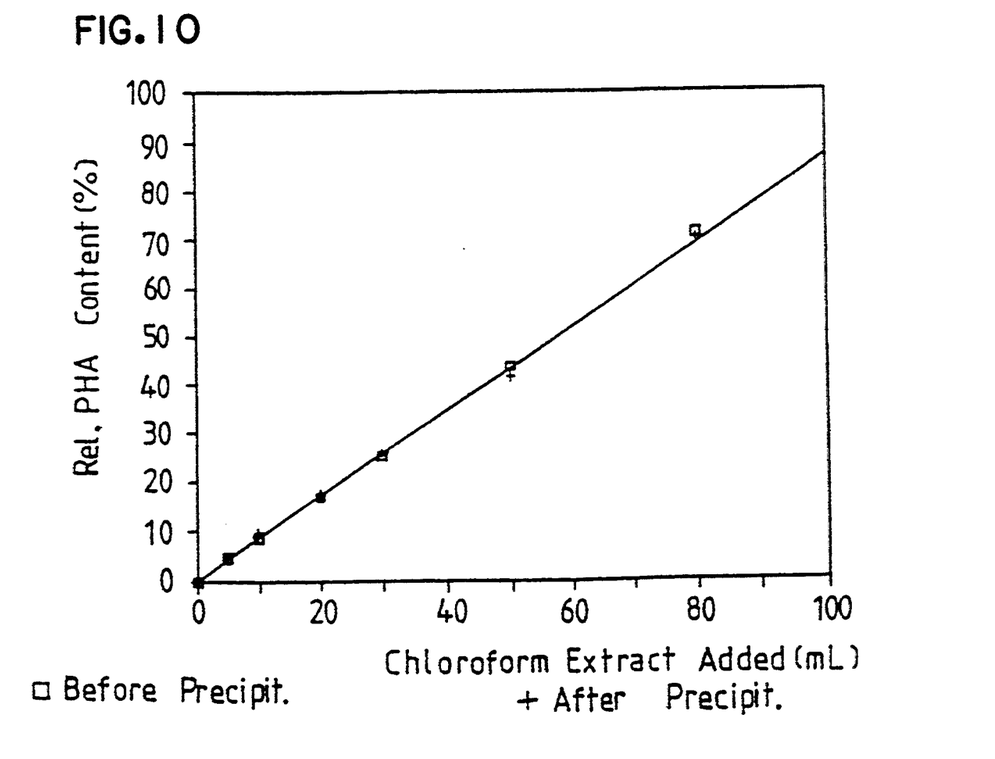
FIG. 10 shows the comparison of the relative content of PHA in the mixed solvent solution and that of blended PHA after precipitation. This shows that PHA copolymer and PHB homopolymer are coprecipitated quantitatively.

Solution blending of PHB and PHA 22 g of dried cells with 75% PHA content, cultured from *Pseudomonas cepacia* KYG-505 (KCCM 10004) in the synthetic medium adopted in Example 1 with the use of sucrose and $(NH_4)_2SO_4$, was extracted with 500 mL of chloroform. The extracted chloroform solution, in a quantity of 0.0, 5, 10, 20, 50, and 80 mL each, was mixed with 10 mL of chloroform solution in which 2 g of PHB was melted, and stirred at 25° C. for an hour. Then methyl alcohol, five times as much as chloroform solution volume, was added to it, left to precipitate, filtered, and dried in vacuum at 100° C., whereby a PHA polymer blend was obtained. The amounts of precipitation according to the varying quantity of the added PHA extract solution are given in FIG. 9, while FIG. 10 shows that, at a time of blending of the solutions, the relative contents both of PHA in the mixed chloroform solution and one in the polymer blend obtained after the precipitation is the same. This means that there was no change in the relative contents of PHA before or after the precipitation, indicating that PHA and PHB both precipitate simultaneously and quantitatively.

We claim:

1. A poly-β-hydroxy alkanoate (PHA) copolymer having a mean molecular weight of at least 10,000 and comprising monomers of the formulae:

(1)

(2)

wherein n is an integer selected from the group consisting of 2, 4, 6, 8 and 10 and m is an integer selected from the group consisting of 0, 2, 4, 6 and 8.

2. The PHA copolymer according to claim 1, wherein said copolymer has a composition of monomers having the following ranges of weight percentages:

3-hydroxy butyrate:0.0 –0.5 wt %
3-hydroxy hexanoate:1.0 –5.0 wt %
3-hydroxy-4-hexenoate:0.0 –1.0 wt %
3-hydroxy octanoate:5.0 –15.0 wt %
3-hydroxy-6-octenoate:0.0 –5.0 wt %
3-hydroxy decanoate:40.0 –60.0 wt %
3-hydroxy-8-decenoate:0.0 –10.0 wt %
3-hydroxy dodecanoate:10.0 –20.0 wt %
3-hydroxy-10-dodecenoate:0.0 –20.0 wt %
3-hydroxy tetradecanoate:0.0 –5.0 wt %
3-hydroxy-12-tetradecenoate:0.0 –5.0 wt %.

3. The PHA copolymer according to claim 1, comprising 3-hydroxy butyrate present in an amount of up to 0.5 percent by weight.

4. The PHA copolymer according to claim 1, comprising 3-hydroxy-4-hexenoate present in an amount of up to 1.0 percent by weight.

5. The PHA copolymer according to claim 1, comprising 3-hydroxy-6-octenoate present in an amount of up to 5.0 percent by weight.

6. The PHA copolymer according to claim 1, comprising 3-hydroxy-8-decenoate present in an amount of up to 10.0 percent by weight.

7. The PHA copolymer according to claim 1, comprising 3-hydroxy-10-dodecenoate present in an amount of up to 20.0 percent by weight.

8. The PHA copolymer according to claim 1, comprising 3-hydroxy tetradecanoate present in an amount of up to 5.0 percent by weight.

9. The PHA copolymer according to claim 1, comprising 3-hydroxy-12-tetradecenoate present in an amount of up to 5.0 percent by weight.

* * * * *